United States Patent
Osumi

(10) Patent No.: US 9,795,364 B2
(45) Date of Patent: Oct. 24, 2017

(54) ULTRASONIC DIAGNOSTIC APPARATUS, MEDICAL IMAGE PROCESSING APPARATUS, AND MEDICAL IMAGE PROCESSING METHOD

(75) Inventor: Ryota Osumi, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 13/308,593

(22) Filed: Dec. 1, 2011

(65) Prior Publication Data

US 2012/0078104 A1 Mar. 29, 2012

Related U.S. Application Data

(63) Continuation of application No. PCT/JP2011/070609, filed on Sep. 9, 2011.

(30) Foreign Application Priority Data

Sep. 9, 2010 (JP) .................................. 2010-202092

(51) Int. Cl.
| | |
|---|---|
| *A61B 8/08* | (2006.01) |
| *G06T 5/00* | (2006.01) |
| *A61B 8/00* | (2006.01) |
| *G01S 7/52* | (2006.01) |
| *G01S 15/89* | (2006.01) |

(52) U.S. Cl.
CPC ............ *A61B 8/5215* (2013.01); *G06T 5/002* (2013.01); *G06T 5/003* (2013.01); *A61B 8/0866* (2013.01);
(Continued)

(58) Field of Classification Search
USPC .................................. 600/437; 382/128, 260
See application file for complete search history.

(56) References Cited

U.S. PATENT DOCUMENTS 6,375,618 B1 * 4/2002 Chiao et al. .................. 600/447
2006/0020203 A1 * 1/2006 Tamura ......................... 600/437
(Continued)

FOREIGN PATENT DOCUMENTS

| CN | 1316227 A | 10/2001 |
|---|---|---|
| CN | 101467897 A | 7/2009 |

(Continued)

OTHER PUBLICATIONS

International Search Report and Written Opinion issued Dec. 13, 2011 in patent application No. PCT/JP2011/070609 with English Translation of Category of Cited Documents.

(Continued)

*Primary Examiner* — Rochelle Turchen
(74) *Attorney, Agent, or Firm* — Oblon, McClelland, Maier & Neustadt, L.L.P.

(57) ABSTRACT

According to one embodiment, an ultrasonic diagnostic apparatus includes an image acquisition unit configured to acquire an ultrasonic image, a first calculation unit which calculates directions of edges in a local region in the ultrasonic image, sizes of the edges in the local region, and directional uniformity of the edges in the local region, a second calculation unit which calculates a composite coefficient by using the sizes of the edges and the directional uniformity of the edges, a third calculation unit which calculates a filtering coefficient for a region corresponding to the local region based on the composite coefficient, and a filtering unit which performs filtering processing for sharpening or smoothing the ultrasonic image with respect to the ultrasonic image by using the filtering coefficient.

13 Claims, 9 Drawing Sheets

(52) U.S. Cl.
CPC ............... *A61B 8/463* (2013.01); *A61B 8/466* (2013.01); *A61B 8/483* (2013.01); *G01S 7/52074* (2013.01); *G01S 7/52077* (2013.01); *G01S 15/8993* (2013.01); *G06T 2207/10132* (2013.01); *G06T 2207/20008* (2013.01)

(56) References Cited

U.S. PATENT DOCUMENTS

| | | | |
|---|---|---|---|
| 2006/0247525 A1* | 11/2006 | Huo et al. | 600/437 |
| 2008/0077011 A1* | 3/2008 | Azuma et al. | 600/443 |
| 2009/0171208 A1* | 7/2009 | Osumi et al. | 600/443 |
| 2009/0177086 A1* | 7/2009 | Steen | A61B 8/0858 600/443 |
| 2010/0228129 A1 | 9/2010 | Osumi | |

FOREIGN PATENT DOCUMENTS

| | | |
|---|---|---|
| CN | 101822547 A | 9/2010 |
| JP | 2008-505675 | 2/2008 |
| JP | 2009-051145 | 3/2009 |
| JP | 2009-153918 | 7/2009 |
| JP | 2010-227554 | 10/2010 |

OTHER PUBLICATIONS

Kazunori Mori, et al., "Segmentation of Color Images Using Texture Features and Clustering Method", Department of Computer Science and Systems Engineering, Faculty of Engineering, Muroran Institute of Technology, Feb. 4, 2003, pp. 83-87 (with English Abstract).

Yasunori Kamiya, et al., "Combining Different Types of Local Features for Generic Object Recognition", D vol. J92-D, No. 5, May 1, 2009, pp. 628-638.

English Translation of International Search Report issued Dec. 13, 2011 in PCT/JP2011/070609.

Combined Search Report and Office Action issued Sep. 12, 2013 in Chinese Patent Application No. 201180002028.3 (with English translation).

* cited by examiner

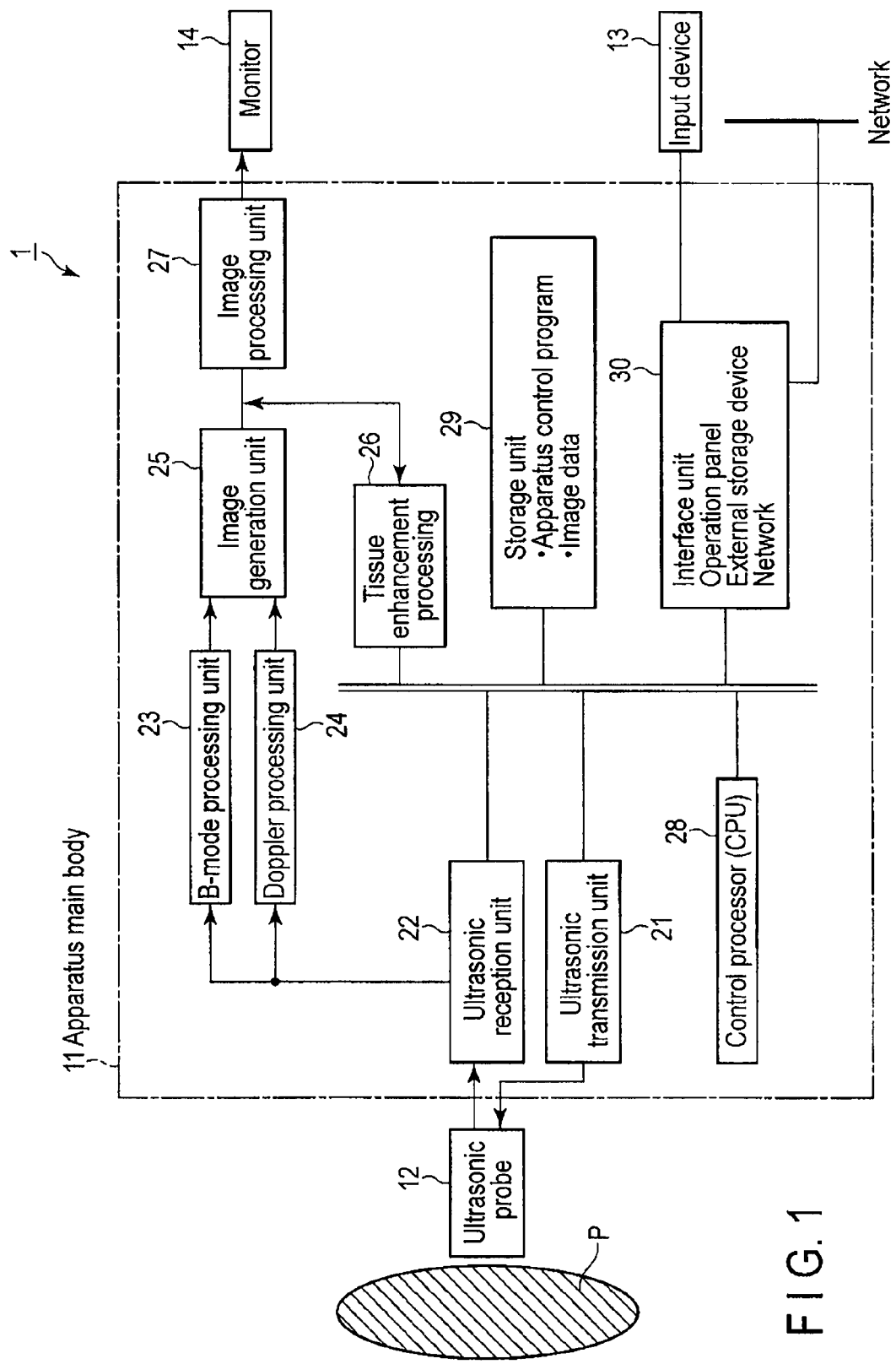
F I G. 1

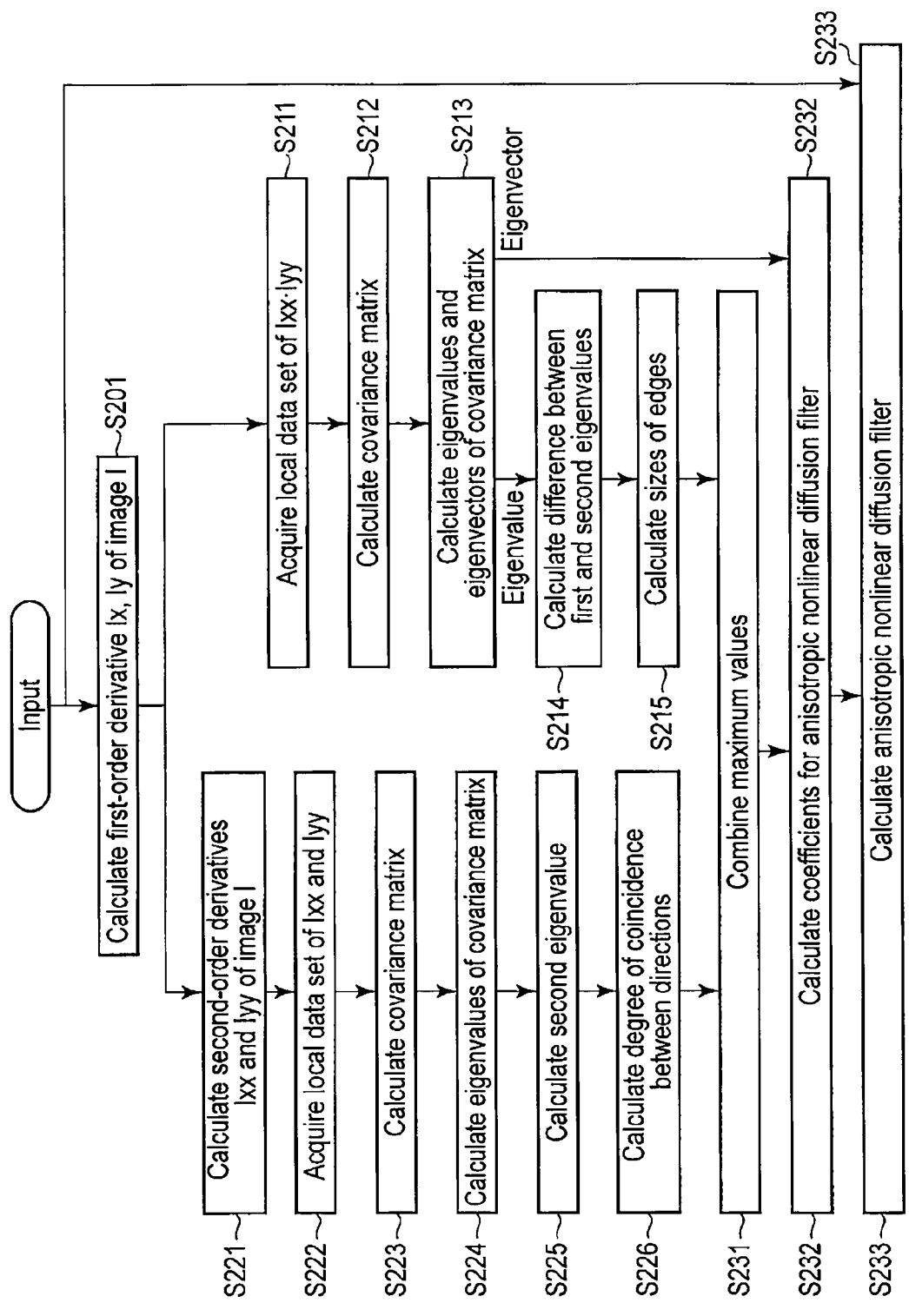
F I G. 3

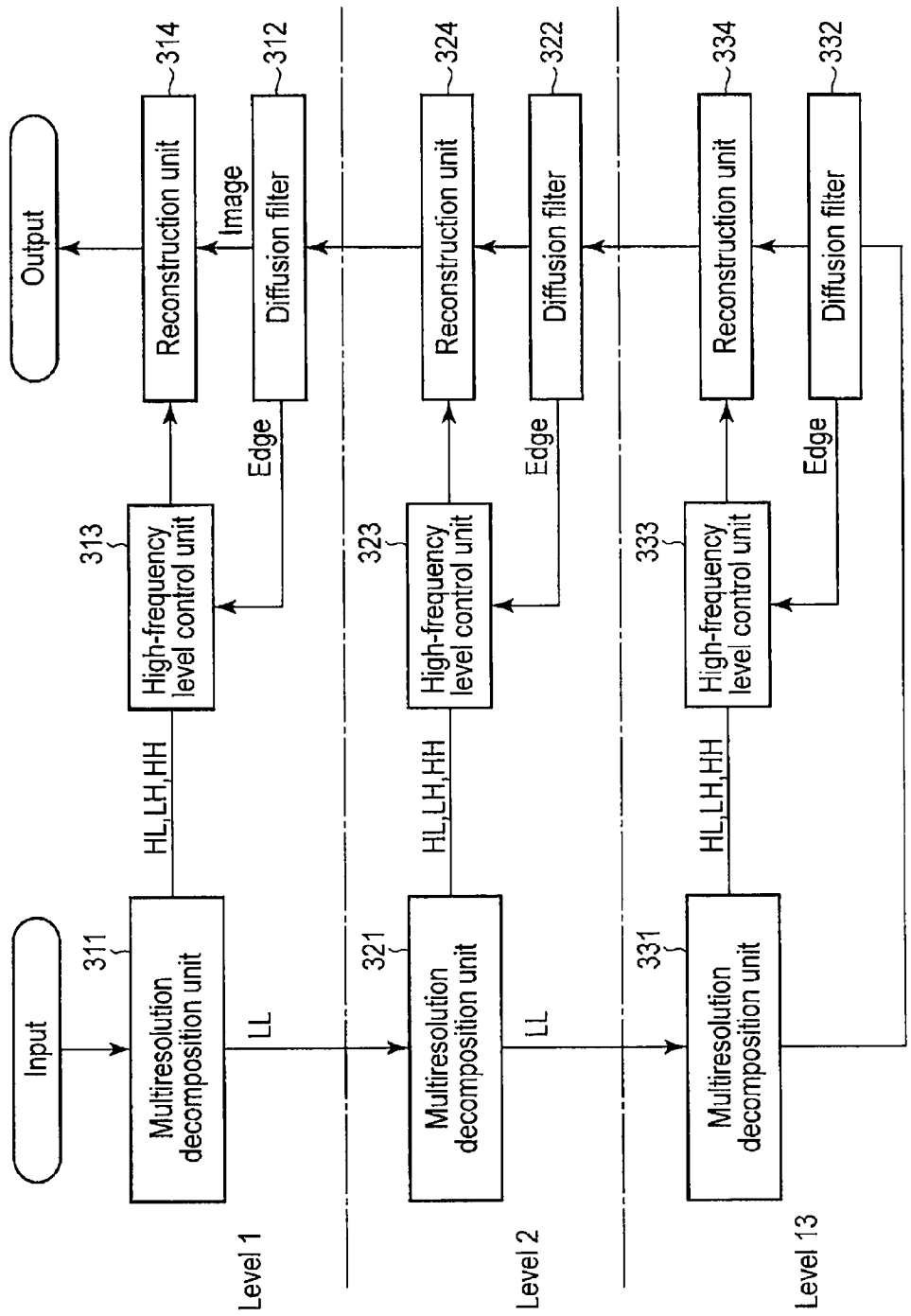
F I G. 5

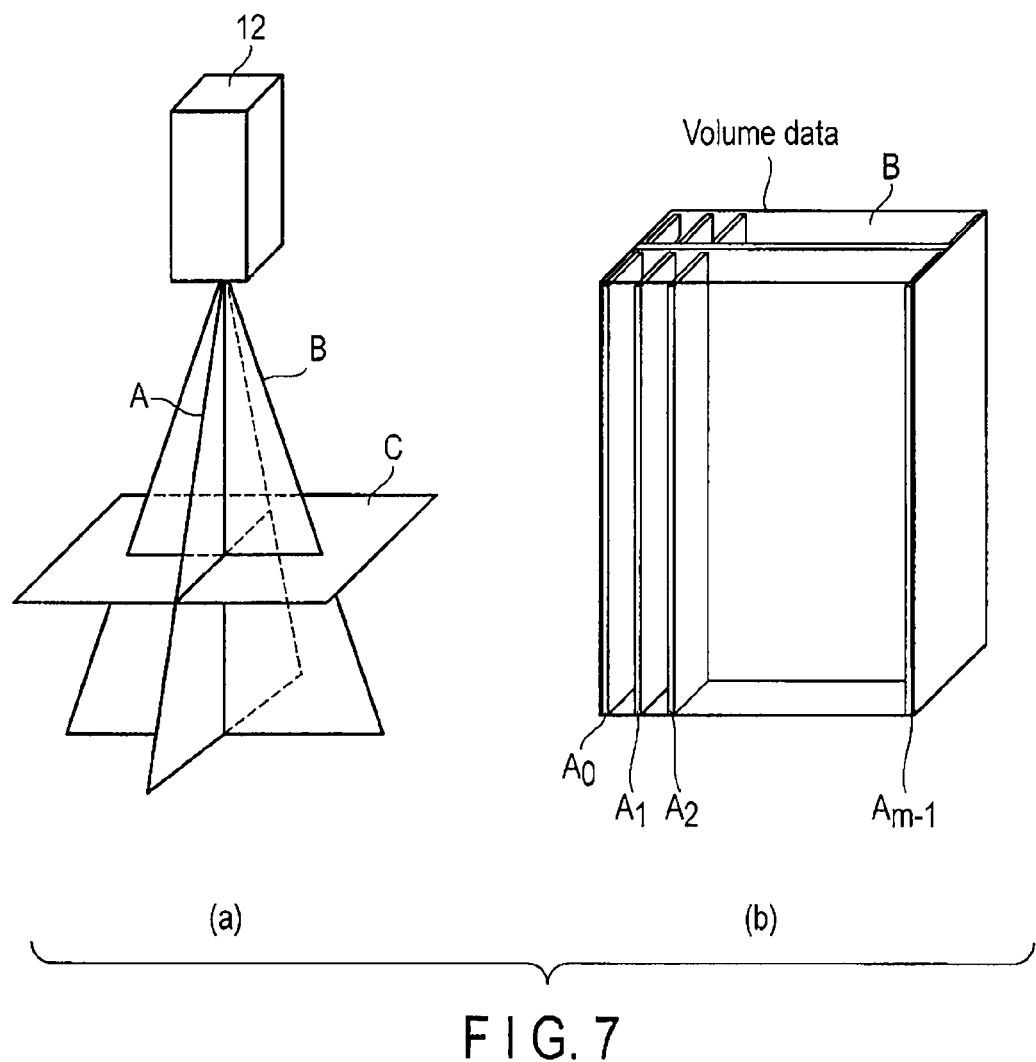
F I G. 7

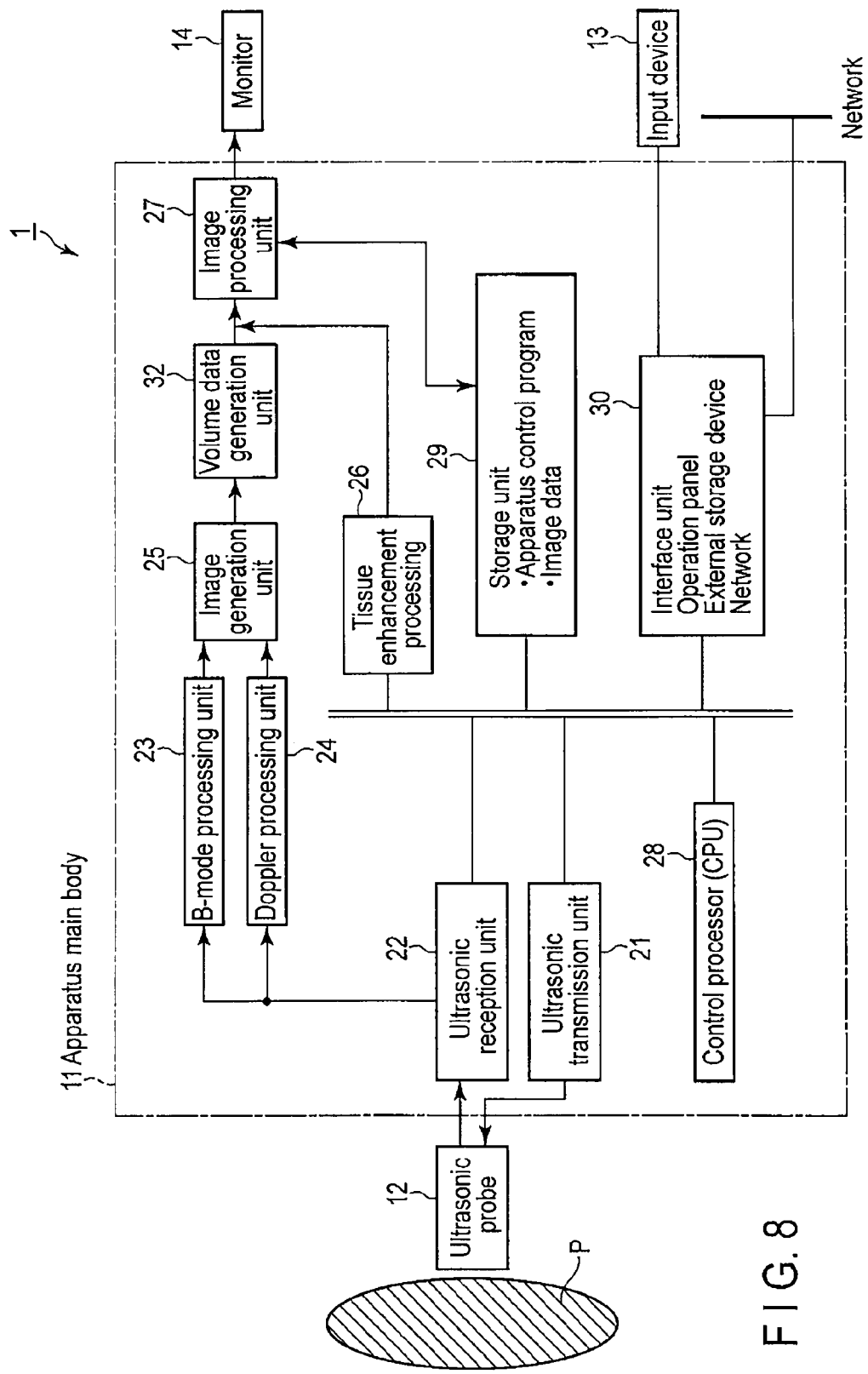
F I G. 8

ULTRASONIC DIAGNOSTIC APPARATUS, MEDICAL IMAGE PROCESSING APPARATUS, AND MEDICAL IMAGE PROCESSING METHOD

CROSS-REFERENCE TO RELATED APPLICATIONS

This application is a Continuation application of PCT Application No. PCT/JP2011/070609, filed Sep. 9, 2011 and based upon and claiming the benefit of priority from prior Japanese Patent Applications No. 2010-202092, filed Sep. 9, 2010; and No. 2011-197698, filed Sep. 9, 2011, the entire contents of all of which are incorporated herein by reference.

FIELD

Embodiments described herein relate generally to an ultrasonic diagnostic apparatus which transmits ultrasonic waves to the inside of an object and obtains diagnostic information in the object based on reflected waves from the inside of the object, and a medical image processing apparatus and medical image processing method which perform image processing for ultrasonic wave data and the like acquired by the ultrasonic diagnostic apparatus.

BACKGROUND

Ultrasonic diagnosis allows to display in real time how the heart beats or the fetus moves, by simply bringing an ultrasonic probe into contact with the body surface. This technique is highly safe, and hence allows repetitive examination. Furthermore, this system is smaller in size than other diagnostic apparatuses such as X-ray, CT, and MRI apparatuses and can be moved to the bedside to be easily and conveniently used for examination. In addition, ultrasonic diagnosis is free from the influences of exposure using X-rays and the like, and hence can be used in obstetric treatment, treatment at home, and the like.

In addition, ultrasonic diagnosis is frequently used in the orthopedic field. For example, ultrasonic diagnosis is used to morphologically diagnose rheumatism and the rupture of tissues upon setting relatively fine tissues such as tendons, muscles, bones, and their surfaces as observation regions. The merit of the use of ultrasonic image diagnosis in the orthopedic field is that it is possible to not only grasp a change in fine structure as described above but also observe the movement of the structure in real time.

The image obtained by an ultrasonic diagnostic apparatus contains various kinds of noise and speckle caused by the interference phenomenon of received ultrasonic signals, which often hinder the accurate observation of the position and shape of the boundary of an object tissue, in addition to information associated with the object tissue. As an image filtering method of reducing such noise and speckle and enhancing information associated with an object tissue, there is available, for example, a method of detecting edge information of an image, smoothing information in the edge direction, and sharpening information in a direction perpendicular to the edge direction. In such a filtering method, when a tissue structure is almost uniform in a specific direction from the viewpoint of a local region like a muscle tissue structure, it is necessary to adjust the respective parameters of the filter so as to sharpen the structure.

CITATION LIST

Patent Literature

Patent Literature 1: Jpn. Pat. Appln. KOKAI Publication No. 2009-153918
Patent Literature 1: Japanese Patent Application No. 2009-51145

BRIEF DESCRIPTION OF THE DRAWINGS

FIG. 1 is a block diagram showing the arrangement of an ultrasonic diagnostic apparatus 1 according to the first embodiment.

FIG. 3 is a flowchart showing a procedure for tissue enhancement filtering processing executed by a tissue enhancement processing unit 26.

FIG. 5 is a view for explaining speckle reduction processing using a tissue enhancement filtering function which is executed by a speckle reduction processing unit 31.

FIG. 7 is a view for explaining a tissue enhancement filtering function according to the third embodiment.

FIG. 8 is a block diagram showing the arrangement of an ultrasonic diagnostic apparatus 1 according to the fourth embodiment.

DETAILED DESCRIPTION

Figure 2:
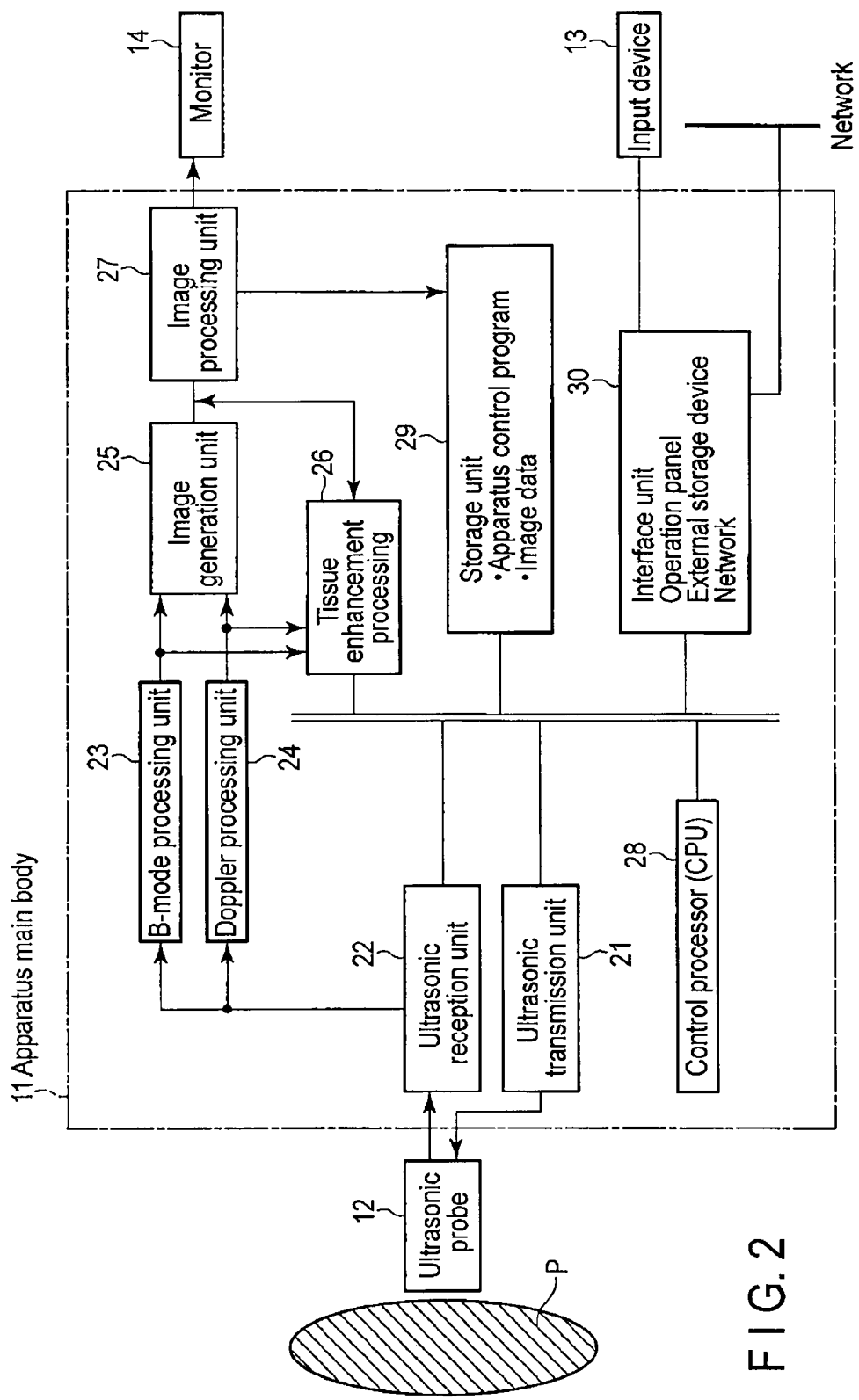
FIG. 2 is a block diagram showing a modification of the arrangement of the ultrasonic diagnostic apparatus 1 according to the first embodiment.

In general, according to one embodiment, an ultrasonic diagnostic apparatus includes an image acquisition unit configured to acquire an ultrasonic image, a first calculation unit which calculates directions of edges in a local region in the ultrasonic image, sizes of the edges in the local region, and directional uniformity of the edges in the local region, a second calculation unit which calculates a composite coefficient by using the sizes of the edges and the directional uniformity of the edges, a third calculation unit which calculates a filtering coefficient for a region corresponding to the local region based on the composite coefficient, and a filtering unit which performs filtering processing for sharpening or smoothing the ultrasonic image with respect to the ultrasonic image by using the filtering coefficient.

The first to fourth embodiments will be described below with reference to the accompanying drawings. Note that the same reference numerals in the following description denote constituent elements having almost the same functions and arrangements, and a repetitive description will be made only when required.

(First Embodiment)

An ultrasonic diagnostic apparatus according to an embodiment includes an image acquisition unit which acquires an ultrasonic image, a first calculation unit which calculates the directions of edges in a local region in an ultrasonic image, the sizes of the edges in the local region, and the directional uniformity of the edges in the local region, a second calculation unit which calculates composite coefficients by using the sizes of the edges and the directional uniformity of the edges, a third calculation unit which calculates filtering coefficients for a region corresponding to the local region based on the composite coefficient, and a filtering unit which performs filtering processing for an ultrasonic image to sharpen or smooth the ultrasonic image by using the filtering coefficients.

The embodiment will be described below with reference to the accompanying drawings. Note that the same reference numerals in the following description denote constituent elements having almost the same functions and arrangements, and a repetitive description will be made only when required.

FIG. 1 is a block diagram showing the arrangement of an ultrasonic diagnostic apparatus 1 according to this embodiment. As shown in FIG. 1, the ultrasonic diagnostic apparatus 1 includes an ultrasonic probe 12, an input device 13, a monitor 14, an ultrasonic transmission unit 21, an ultrasonic reception unit 22, a B-mode processing unit 23, a Doppler processing unit 24, an image generation unit 25, a tissue enhancement processing unit 26, an image processing unit 27, a control processor (CPU) 28, a storage unit 29, and an interface unit 30. The function of each constituent element will be described below.

The ultrasonic probe 12 is a device (probe) which transmits ultrasonic waves to an object and receives reflected waves from the object based on the transmitted ultrasonic waves. The ultrasonic probe 12 has, on its distal end, an array of a plurality of piezoelectric transducers, a matching layer, a backing member, and the like. The piezoelectric transducers of the ultrasonic probe 12 transmit ultrasonic waves in a desired direction in a scan region based on driving signals from the ultrasonic transmission unit 21 and convert reflected waves from the object into electrical signals. The matching layer is an intermediate layer which is provided for the piezoelectric transducers to make ultrasonic energy efficiently propagate. The backing member prevents ultrasonic waves from propagating backward from the piezoelectric transducers. When the ultrasonic probe 12 transmits an ultrasonic wave to an object P, the transmitted ultrasonic wave is sequentially reflected by a discontinuity surface of acoustic impedance of internal body tissue, and is received as an echo signal by the ultrasonic probe 12. The amplitude of this echo signal depends on an acoustic impedance difference on the discontinuity surface by which the echo signal is reflected. The echo produced when a transmitted ultrasonic pulse is reflected by the surface of a moving blood flow, cardiac wall, or the like is subjected to a frequency shift depending on the velocity component of the moving body in the ultrasonic transmission direction due to the Doppler effect.

The input device 13 is connected to an apparatus body 11 and includes various types of switches, buttons, a trackball 13s, a mouse 13c, and a keyboard 13d which are used to input, to the apparatus body 11, various types of instructions, conditions, an instruction to set a region of interest (ROI), various types of image quality condition setting instructions, and the like from an operator. When, for example, the operator operates the end button or FREEZE button of the input device 13, the transmission/reception of ultrasonic waves is terminated, and the ultrasonic diagnostic apparatus is set in a pause state.

The monitor 14 displays morphological information and blood flow information in the living body as images based on video signals from the image processing unit 27.

The ultrasonic transmission unit 21 includes a trigger generation circuit, delay circuit, and pulser circuit (none of which are shown). The pulser circuit repetitively generates rate pulses for the formation of transmission ultrasonic waves at a predetermined rate frequency fr Hz (period: 1/fr sec). The delay circuit gives each rate pulse a delay time necessary to focus an ultrasonic wave into a beam and determine transmission directivity for each channel. The trigger generation circuit applies a driving pulse to the probe 12 at the timing based on this rate pulse.

The ultrasonic transmission unit 21 has a function of instantly changing a transmission frequency, transmission driving voltage, or the like to execute a predetermined scan sequence in accordance with an instruction from the control processor 28. In particular, the function of changing a transmission driving voltage is implemented by linear amplifier type transmission circuit capable of instantly switching its value or a mechanism of electrically switching a plurality of power supply units.

The ultrasonic reception unit 22 includes an amplifier circuit, A/D converter, and adder (none of which are shown). The amplifier circuit amplifies an echo signal received via the probe 12 for each channel. The A/D converter gives the amplified echo signals delay times necessary to determine reception directivities. The adder then performs addition processing for the signals. With this addition, a component reflected from a direction corresponding to the reception directivity of the echo signal is enhanced to form a composite beam for ultrasonic transmission/reception in accordance with reception directivity and transmission directivity.

The B-mode processing unit 23 receives an echo signal from the ultrasonic transmission unit 21, and performs logarithmic amplification, envelope detection processing, and the like for the signal to generate data whose signal intensity is expressed by a luminance level. This data is transmitted to the image generation unit 25, and is displayed on the monitor 14 as a B-mode image whose reflected wave intensity is expressed by a luminance.

The Doppler processing unit 24 frequency-analyzes velocity information from the echo signal received from the ultrasonic transmission unit 21 to extract a blood flow, tissue, and contrast medium echo component by the Doppler effect, and obtains blood flow information such as an average velocity, variance, and power at multiple points. The obtained blood flow information is sent to the image generation circuit 25, and is displayed in color as an average velocity image, a variance image, a power image, and a combined image of them on the monitor 14.

The image generation unit 25 combines a scanning line signal string for ultrasonic scanning with character information of various types of parameters, scale marks, and the like received from the B-mode processing unit 23, the Doppler processing unit 24, and the speckle reduction processing unit 26, and generates an ultrasonic diagnostic image as a display image by converting (scan conversion) the scanning line signal string into a scanning line signal string in a general video format typified by a TV format. The image generation unit 25 includes a memory to store image data, and allows the operator to call up an image recorded during examination after diagnosis. Note, that data before it is input to the image generation unit 25 is, for example, a set of amplitude values or luminance values at the respective spatial positions and called "raw data".

The tissue enhancement processing unit 26 executes processing based on a tissue enhancement filtering function (to be described later) for the ultrasonic image generated by the image generation unit 25 under the control of the control processor 28.

The control processor 28 has a function as an information processing apparatus (computer), and controls the operation of this ultrasonic diagnostic apparatus main body. The control processor 28 reads out a dedicated program for implementing the tissue enhancement filtering function (to be described later) from the storage unit 29, expands the program in the memory of the processor, and executes computation/control and the like associated with various types of processing.

The storage unit 29 stores a dedicated program for implementing the tissue enhancement filtering function (to be described), diagnosis information (patient ID, findings by doctors, and the like), a diagnostic protocol, transmission/reception conditions, a program for implementing a speckle reduction function, a body mark generation program, and other data. The storage unit 29 is also used to store images in the image memory 26, as needed. It is possible to transfer data in the storage unit 29 to an external peripheral device via the interface unit 30.

The interface unit 30 is an interface associated with the input device 13, a network, and a new external storage device (not shown). The interface unit 30 can transfer data such as ultrasonic images, analysis results, and the like obtained by this apparatus to another apparatus via a network.

(Tissue Enhancement Filtering Function)

The tissue enhancement filtering function of this ultrasonic diagnostic apparatus will be described next. This function calculates not only the sizes of edges of an ultrasonic image but also the uniformity of the edges by performing, for example, principal component analysis of a local region of second-order derivatives of the ultrasonic image, and executes filtering processing in accordance with the directions of the edges by using the information associated with the sizes of the edges and the uniformity of the edges. This can acquire an ultrasonic image with a tissue (muscle tissue) such as a tendon, muscle, or bone being enhanced and unnatural patterns on portions other than the muscle tissue being reduced.

Note the following description will exemplify a case in which processing (tissue enhancement filtering processing) based on the tissue enhancement filtering function is executed for the ultrasonic image generated by the image generation unit 25. However, the present embodiment is not limited to this, and it is possible to execute tissue enhancement filtering processing for raw data before it is input to the image generation unit 25. FIG. 2 is a block diagram showing the arrangement of the ultrasonic diagnostic apparatus 1 in such a case.

FIG. 3 is a flowchart showing a procedure for tissue enhancement filtering processing executed by the tissue enhancement processing unit 26. The contents of processing executed in each step will be described below.

[Calculation of Gradient Vector $I_x$, $I_y$: Step S201]

First of all, the tissue enhancement processing unit 26 calculates spatial derivatives (i.e., a gradient vector $(I_x, I_y)$) of the image received from the image generation unit 25 in the x (horizontal) direction and the y (vertical) direction (step S201).

[Calculation of Size of Edge: Steps S211 to S215]

The tissue enhancement processing unit 26 then calculates the size of an edge in steps S211 to S215. The tissue enhancement processing unit 26 acquires a local data set about the respective pixels of the gradient vector $(I_x, I_y)$ and their surroundings (step S211), and calculates the covariance matrix of the acquired data set (step S212). If the range of the local data set of the spatial derivative $(I_x, I_y)$ of the input image is (M·M) pixels, and the number of elements is N=M·M, a covariance matrix S of the data is given by $$S = \frac{1}{N}\sum_{n=1}^{N}\begin{pmatrix} (I_{xn}-E(I_x))^2 & (I_{xn}-E(I_x))(I_{yn}-\overline{I_y}) \\ (I_{xn}-E(I_x))(I_{yn}-E(I_y)) & (I_{yn}-E(I_y))^2 \end{pmatrix} = \quad (1)$$

$$\begin{pmatrix} s_{11} & s_{12} \\ s_{12} & s_{22} \end{pmatrix}$$

where $E(I_x)$ and $E(I_y)$ are the expected values of $I_x$ and $I_y$.

The tissue enhancement processing unit 26 calculates a combination of the eigenvalues and eigenvectors of the covariance matrix (step S213), calculates the difference between the first and second eigenvalues of the combination of the obtained eigenvalues (step S214), and calculates the size of the edge from the difference (step S215).

When calculating the eigenvalues and eigenvectors of the covariance matrix, the first principal component in principal component analysis is an eigenvector belonging to the first eigenvalue of the covariance matrix, and represents the direction of the edge. The first eigenvalue represents the size of the edge of the image. It is possible to express the size of the edge by calculating the difference between the first eigenvalue and another eigenvalue (the second eigenvalue when the image is a two-dimensional image). In this embodiment, however, the size $(P_E)$ of the edge is calculated by, for example, equation (2) so as to fall within the range of 0 to 1.

$$P_E = 1 - \exp\left(-\frac{(\lambda_{S1}-\lambda_{S2})^2}{k^2}\right) \quad (2)$$

where $\lambda_{S1}$ and $\lambda_{S2}$ are eigenvalues of the covariance matrix, and k is a parameter for adjusting edge enhancement. For example, reducing the value of k can further enhance the edge. The eigenvalue of the covariance matrix provides information associated with the direction of an anisotropic nonlinear diffusion filter at the stage (to be described later).

[Calculation of Uniformity of Edges: Steps S221 to S226]

The tissue enhancement processing unit 26 calculates the uniformity of the edges in steps S221 to S226. That is, the tissue enhancement processing unit 26 further executes spatial differentiation for each pixel of the gradient vector $(I_x, I_y)$ to calculates second-order derivative components (step S221). Assume that spatial differentiation in this case calculates a derivative $I_{xx}$ of $I_x$ in the x direction and a derivative $I_{yy}$ of $I_y$ in the y direction. Calculating second-order derivatives of the image in this manner can detect the uniformity of edges more clearly as compared with when calculating first-order derivatives.

The tissue enhancement processing unit 26 acquires a local data set around the gradient vector $(I_x, I_y)$ (step S222), and calculates the covariance matrix of the data set (step S223). The tissue enhancement processing unit 26 calculates an eigenvalue and the second eigenvalue of the calculated covariance matrix (steps S224 and S225), and calculates the directional uniformity of the edges from the obtained second eigenvalue.

The following is the reason why the second eigenvalue is used to calculate the directional uniformity of the edges. That is, obtaining a principal component by performing principal component analysis on the data set of a local region of a vector space is equivalent to minimizing the square means projection error of the data set with respect to a principal subspace. This square means projection error with respect to the principal subspace represents directional uniformity relative to the principal component direction. The square means projection error with respect to the principal subspace is the sum of eigenvalues associated with eigenvectors perpendicular to the principal subspace, and is equal to the second eigenvalue when the image is a two-dimensional image. Calculating the second eigenvalue of the covariance matrix with respect to a local region of $(I_{xx}, I_{yy})$ in this manner can detect directional uniformity relative to the principal component direction, i.e., the edge direction. Note, however, that in this embodiment, directional uniformity ($P_U$) takes the value obtained by subtracting 1 from the contribution ratio of the second eigenvalue so as to fall within the range of 0 to 1, as indicated by equation (3) given below:

$$P_U = 1 - \frac{\lambda_{S2}}{\lambda_{S1} + \lambda_{S2}} \quad (3)$$

[Anisotropic Nonlinear Diffusion Filtering Processing: Steps S231 to S233]

The tissue enhancement processing unit 26 then executes anisotropic nonlinear diffusion filtering processing in steps S231 to S233. That is, the tissue enhancement processing unit 26 executes combining processing by calculating a maximum value for each pixel by using the sizes of the edges calculated in step S215 and the directional uniformity calculated in step S226 (step S231). The object of calculating the maximum values of edge sizes and directional uniformity for each pixel is to perform the same filtering processing for both "edge" and "a tissue whose structure is uniform in a specific direction". Calculating the sums of the size of the edge and directional uniformity for each pixel instead of this processing can obtain a similar effect.

The tissue enhancement processing unit 26 then calculates coefficients for an anisotropic nonlinear diffusion filter by using the obtained maximum values (step S232), and executes the calculation of an anisotropic nonlinear diffusion filter (i.e., filtering processing) by using the calculated coefficients (step S233).

Note that the anisotropic nonlinear diffusion filter is a filter obtained by solving the diffusion equation given below:

$$\frac{\partial I}{\partial t} = div[D \nabla I] \quad (4)$$

where $I$ is an input image, $\nabla I$ is the gradient vector $(I_x, I_y)$ of the image, $t$ is "time" in a physical phenomenon, which is associated with the repetition number of this processing, and $D$ is a diffusion tensor, whose each element can be expressed by equation (5) given below, with eigenvalues $\lambda_{D1}$ and $\lambda_{D2}$ and eigenvectors $\omega_{D1} = (\cos\phi, \sin\phi)^T$ and $\omega_{D2} = (-\sin\phi, \cos\phi)^T$:

$$D = \begin{pmatrix} d_{11} & d_{12} \\ d_{12} & d_{22} \end{pmatrix} = (\omega_{D1} \; \omega_{D2}) \begin{pmatrix} \lambda_{D1} & 0 \\ 0 & \lambda_{D2} \end{pmatrix} \begin{pmatrix} \omega_{D1} \\ \omega_{D2} \end{pmatrix} \quad (5)$$

The anisotropic nonlinear diffusion filter diffuses the image in the respective directions indicated by the eigenvectors with the diffusivities indicated by eigenvalues associated with the respective directions. In step S232, the tissue enhancement processing unit 26 calculates eigenvalues from the results obtained by combining the sizes of the edges and the directional uniformities by using the directions of the edges of the image, which have already been obtained, as the eigenvectors of the diffusion filter.

Note that the tissue enhancement processing unit 26 calculates the anisotropic nonlinear diffusion filter in step S232 by using a numerical analytical approach based on a known partial differential equation. That is, consider a given point at "time" t. In this case, the tissue enhancement processing unit 26 obtains the new pixel level of this point at "time" t+Δt from the pixel levels of the pixel and its surrounding pixels, for example, nine pixels, and the respective element values of the diffusion tensor. The tissue enhancement processing unit 26 then repeats the same calculation one to several times upon setting t+Δt as new t.

This embodiment uses the principal component analysis method to obtain the sizes and directions of edges. However, the embodiment is not limited to this example, and can use a method of calculating the structure tensor of an image. The structure tensor of an image I is defined as follows:

$$S = G_\rho * \begin{pmatrix} I_x^2 & I_x I_y \\ I_x I_y & I_y^2 \end{pmatrix} = \begin{pmatrix} G_\rho * I_x^2 & G_\rho * (I_x I_y) \\ G_\rho * (I_x I_y) & G_\rho * I_y^2 \end{pmatrix} = \begin{pmatrix} s_{11} & s_{12} \\ s_{12} & s_{22} \end{pmatrix} \quad (6)$$

where $I_x$ and $I_y$ are spatial derivatives of the image I in the x (horizontal) direction and the y (vertical) direction, $G_\rho$ is a two-dimensional Gaussian function, and the operator "*" represents convolution.

When calculating the eigenvalues and eigenvectors of the structure tensor, an eigenvector belonging to the first eigenvalue represents the direction of the edge, and the first eigenvalue represents the size of the edge of the image. In addition, when calculating the directional uniformity of edges, it is possible to obtain the directional uniformity from the second eigenvalues of the structure tensor of the first-order derivatives of the image I defined from the second-order derivatives of the image I.

(Effect)

The ultrasonic diagnostic apparatus described above obtains not only the sizes of edges but also the directional uniformity of them, and then calculates maximum values of both the size and the directional uniformity for each pixel, thereby calculating the diffusivities of the anisotropic nonlinear diffusion filter in accordance with the directions of the edges. This makes it possible to perform proper filtering for a tissue whose structure is uniform in a specific direction and other tissues as compared with when simply calculating diffusivity from the sizes of edges. This can acquire an ultrasonic image with a tissue (muscle tissue) such as a tendon, muscle, or bone being enhanced (sharpened) and unnatural patterns on portions other than the muscle tissue being reduced (smoothed).

(Second Embodiment)

The first embodiment has exemplified the case in which the tissue enhancement filtering function is applied to ultrasonic image data itself to sharpen or smooth the image. In contrast to this, the second embodiment will exemplify a case in which an image is multiresolution-decomposed, and the tissue enhancement filtering function described in the first embodiment is applied to a signal or data at each decomposition level.

Note that Jpn. Pat. Appln. KOKAI Publication No. 2009-153918 discloses the case in which an image is multiresolution-decomposed, and anisotropic nonlinear diffusion filtering is performed at each decomposition level.

Figure 4:
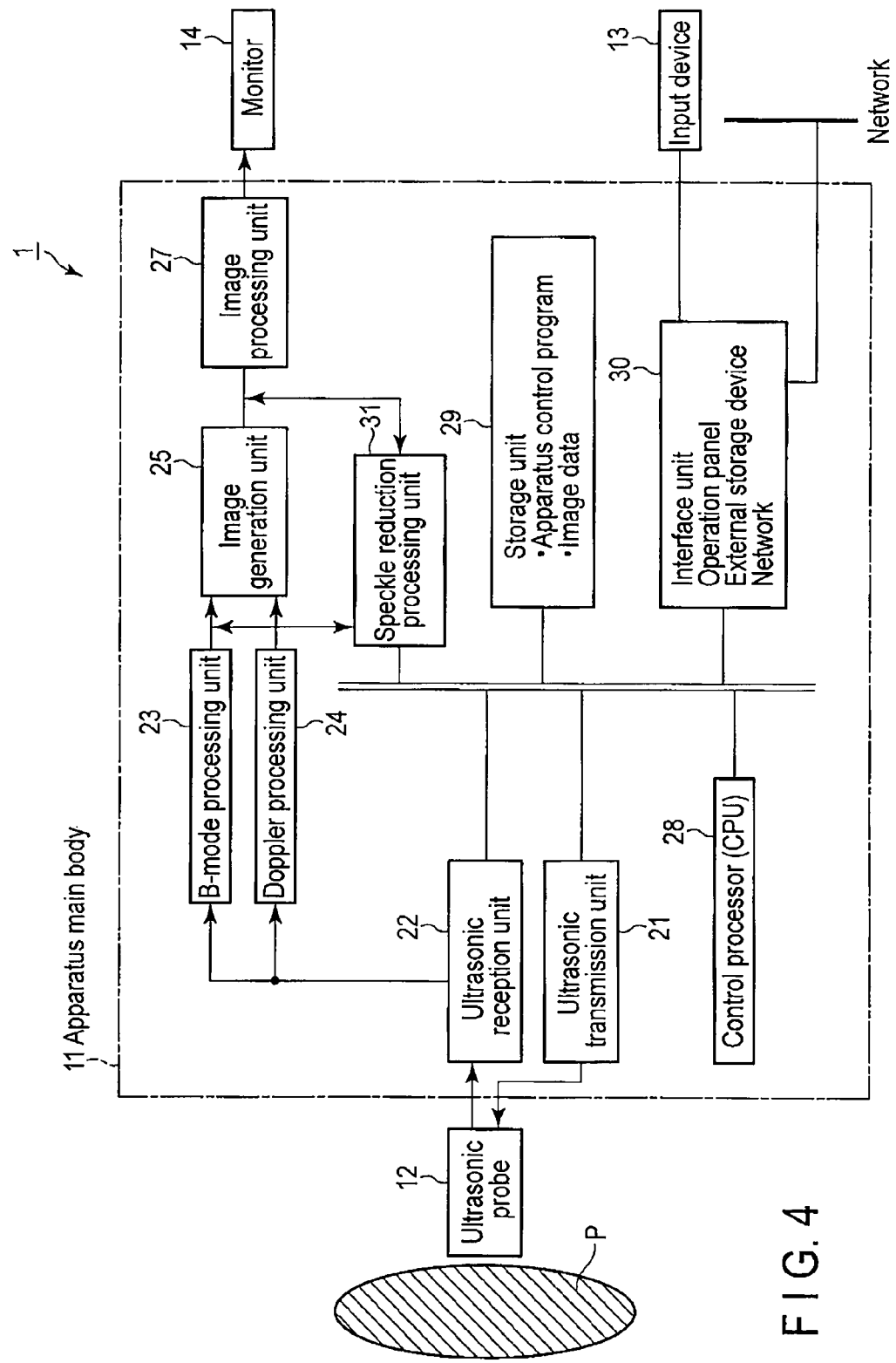
FIG. 4 is a block diagram showing the arrangement of an ultrasonic diagnostic apparatus according to the second embodiment.

FIG. 4 is a block diagram showing the arrangement of an ultrasonic diagnostic apparatus according to the second embodiment. This arrangement differs from that shown in FIG. 1 in that a speckle reduction processing unit 31 replaces the tissue enhancement processing unit 26.

As shown in FIG. 5, a speckle reduction processing unit 32 includes: a multiresolution decomposition unit 311, a diffusion filter 312, a high-frequency level control unit 313, and a reconstruction unit 314 at level 1; a multiresolution decomposition unit 321, a diffusion filter 322, a high-frequency level control unit 323, and a reconstruction unit 324 at level 2; and a multiresolution decomposition unit 331, a diffusion filter 332, a high-frequency level control unit 333, and a reconstruction unit 334 at level 3.

The multiresolution decomposition units 311, 321, and 331 sequentially multiresolution-decompose input raw data or image data from level 1. It is possible to use, for example, discrete wavelet transform, the Laplacian pyramid method, or the like as a multiresolution decomposition technique. This multiresolution decomposition decomposes an image into a low-frequency image (LL), horizontal high-frequency image (LH), vertical high-frequency image (HL), and diagonal high-frequency image (HH) each having a length and a width which are half of those before decomposition. Note that the number of levels (orders) of multiresolution decomposition is not specifically limited. For the sake of a concrete explanation, in this embodiment, the maximum order of multiresolution decomposition is level 3.

The diffusion filters 312, 322, and 332 respectively execute the tissue enhancement filtering processing described in the first embodiment for the input raw data or image data.

The high-frequency level control units 313, 323, and 333 respectively control the horizontal high-frequency image (LH), vertical high-frequency image (HL), and diagonal high-frequency image (HH) input from the multiresolution decomposition units 311, 321, and 331 in accordance with the sizes of edges input from the diffusion filters 312, 322, and 332. Note that the sizes of the edges are, for example, the same as those output in step S215 in FIG. 3.

The reconstruction units 314, 324, and 334 each reconstruct one composite image from one low-frequency image received from each of the diffusion filters 312, 322, and 332 and three high-frequency images received from each of the high-frequency level control units 313, 323, and 333. The length and width of each reconstructed image are twice those of the input image. Note that reconstruction processing can use, for example, discrete wavelet inverse transform when multiresolution decomposition is performed by discrete wavelet transform, and computation inverse to the Laplacian pyramid method when multiresolution decomposition is performed by the Laplacian pyramid method.

The speckle reduction processing unit 31 executes, for example, the following speckle reduction processing. First of all, the multiresolution decomposition unit 311 decomposes input raw data or image data into a low-frequency image (LL), horizontal high-frequency image (LH), vertical high-frequency image (HL), and diagonal high-frequency image (HH), and outputs the low-frequency image (LL) to the multiresolution decomposition unit 321, and the horizontal high-frequency image (LH), vertical high-frequency image (HL), and diagonal high-frequency image (HH) to the high-frequency level control unit 313.

The multiresolution decomposition unit 311 further decomposes the input low-frequency image (LL) into a low-frequency image (LL), horizontal high-frequency image (LH), vertical high-frequency image (HL), and diagonal high-frequency image (HH), and outputs the low-frequency image (LL) to the multiresolution decomposition unit 331, and the horizontal high-frequency image (LH), vertical high-frequency image (HL), and diagonal high-frequency image (HH) to the high-frequency level control unit 323. The multiresolution decomposition unit 311 also executes the same processing for the input low-frequency image (LL).

At level 3, the multiresolution decomposition unit 331 outputs the low-frequency image (LL) acquired by decomposition to the diffusion filter 332. The diffusion filter 332 executes tissue enhancement filtering processing exemplified in the first embodiment by using the low-frequency image (LL). The reconstruction unit 334 reconstructs one image from the low-frequency image (LL) from the diffusion filter 332 and the horizontal high-frequency image (LH), vertical high-frequency image (HL), and diagonal high-frequency image (HH) from the high-frequency level control unit 333. The length and width of the image obtained as a result of reconstruction are twice those of the input image.

At level 2, the diffusion filter 322 receives the reconstructed image from the reconstruction unit 334, executes tissue enhancement filtering processing, and outputs the resultant image to the reconstruction unit 324. On the other hand, the high-frequency level control unit 323 executes high-frequency level control on each high-frequency image output from the multiresolution decomposition unit 321 based on the edges received from the diffusion filter 322. The reconstruction unit 324 reconstructs one image from one low-frequency image from the diffusion filter 322 and three high-frequency images from the high-frequency level control unit 323.

At level 1, substantially the same processing as that at level 2 is executed. As a result, the reconstruction unit 314 outputs the reconstructed image for which tissue enhancement filtering processing has been executed at each decomposition level of multiresolution decomposition. The image obtained in this manner has undergone proper filtering processing applied to a tissue whose structure is uniform in a specific direction and other tissues at each level. Therefore, the tissue is enhanced while unnatural patterns on portions other than the muscle tissue are reduced (smoothed). In addition, multiresolution decomposition allows to perform higher speed and more efficient processing by sequentially performing processing from global processing to local processing.

Note that this embodiment can use horizontal and vertical high-frequency components from the multiresolution decomposition unit instead of the spatial derivative ($I_x$, $I_y$) of an input image. In addition, the embodiment is based on the premise that the anisotropic nonlinear diffusion filters at the respective levels independently calculate spatial derivatives. It is, however, possible to calculate edge information from an input image before multiresolution decomposition and then calculate coefficients for anisotropic nonlinear diffusion filters by reducing and re-sampling them to the image sizes at the respective levels.

(Third Embodiment)

The first and second embodiments have exemplified the case in which speckle reduction processing is executed for two-dimensional image data (or two-dimensional raw data). In contrast to this, an ultrasonic diagnostic apparatus 1 according to this embodiment executes tissue enhancement filtering processing for three-dimensional volume data. For the sake of a concrete explanation, the embodiment will exemplify a case in which tissue enhancement filtering processing is executed for three-dimensional volume data based on raw data before scan conversion processing. However, the embodiment is not limited to this example and can be applied to three-dimensional volume data based on ultrasonic image data after scan conversion processing.

Figure 6:
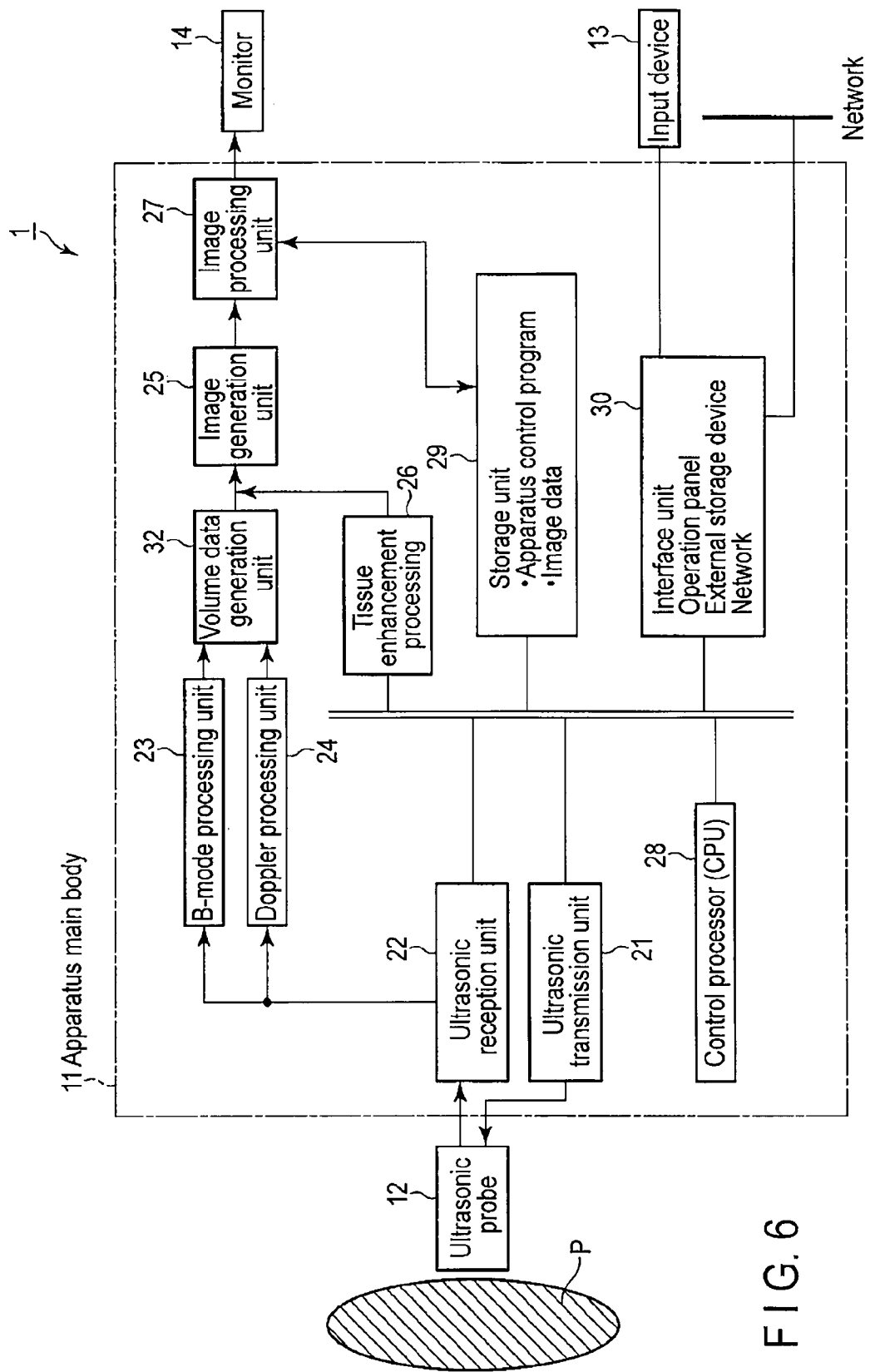
FIG. 6 is a block diagram showing the arrangement of an ultrasonic diagnostic apparatus 1 according to the third embodiment.

FIG. 6 shows the arrangement of the ultrasonic diagnostic apparatus 1 according to this embodiment. This arrangement differs from that shown in FIG. 1 in that it further includes a volume data generation unit 32, a tissue enhancement processing unit 26 performs tissue enhancement filtering processing for volume data from the volume data generation unit 32, and an image processing unit 27 executes volume rendering processing and the like.

The volume data generation unit 32 generates B-mode volume data by using the B-mode image data received from a B-mode processing unit 23. A volume data generation unit 31 generates Doppler mode image volume data by using the Doppler mode data received from a Doppler processing unit 24.

The image processing unit 27 performs predetermined image processing such as volume rendering, multi planar reconstruction (MPR), or maximum intensity projection (MIP) for the B-mode volume data having undergone speckle reduction processing which is received from the image generation unit 25, or the speckle reduction processing unit 26.

FIGS. 7(a) and 7(b) are views for explaining a tissue enhancement filtering function according to this embodiment. As shown in FIG. 7(a), of the cross-sections of volume data, two planes which intersect the central axis of a target region (ultrasonic scanning region) of ultrasonic scanning executed by using an ultrasonic probe 12 and are perpendicular to each other are defined as A plane and B plane, and a plane perpendicular to the central axis and A and B planes is defined as C plane.

The tissue enhancement processing unit 26 receives, for example, B-mode volume data from the volume data generation unit 32. As shown in FIG. 7(b), this volume data can be considered as a set of m planes $A_0, A_1, \ldots, A_{m-1}$ parallel to A plane (i.e., a set of two-dimensional image data parallel to A plane). The tissue enhancement processing unit 26 performs tissue enhancement filtering processing described in the first embodiment for all the two-dimensional image data parallel to A plane. At this time, since a spatial derivative ($I_x, I_y, I_z$) (($I_{xx}, I_{yy}, I_{zz}$ in the case of second order) of the input image is a three-dimensional vector, a local covariance matrix or structure tensor is a 3×3 matrix. When calculating edge information, the tissue enhancement processing unit 26 handles first to third eigenvalues and eigenvectors. In this case, although it is preferable to calculate the size of each edge from the difference between the first eigenvalue and the third eigenvalue, it is preferable to calculate the directional uniformity of edges from the sum of eigenvalues other than first eigenvalues, i.e., the sum of second and third eigenvalues.

The image generation unit 25 generates volume data based on ultrasonic image data by executing scan conversion and the like for two-dimensional image data forming the volume data to which tissue enhancement filtering processing has been executed. The image processing unit 27 receives volume data from the image generation unit 25, and executes predetermined image processing such as volume rendering, multi planar reconstruction (MPR), or maximum intensity projection (MIP) based on these data. A monitor 14 displays the three-dimensional image data generated by this image processing in a predetermined form.

The ultrasonic diagnostic apparatus according to this embodiment can enhance, in overall B-mode volume data, a tissue while reducing unnatural patterns on portions other than the muscle tissue by performing tissue enhancement filtering processing for all the two-dimensional image data forming the B-mode volume data. As a consequence, it is possible to generate suitable ultrasonic images in association with not only A plane but also B and C planes as arbitrary cross-sections.

(Fourth Embodiment)

The third embodiment has exemplified the case in which tissue enhancement filtering processing is executed for B-mode volume data before three-dimensional image processing. In contrast to this, an ultrasonic diagnostic apparatus 1 according to this embodiment executes tissue enhancement filtering processing for image data after three-dimensional image processing.

FIG. 8 shows the arrangement of the ultrasonic diagnostic apparatus 1 according to this embodiment. This arrangement differs from that shown in FIG. 6 in that a volume data generation unit 32 is provided on the subsequent stage of an image generation unit 25, and a tissue enhancement processing unit 26 performs tissue enhancement filtering processing for data after scan conversion.

Figure 9:
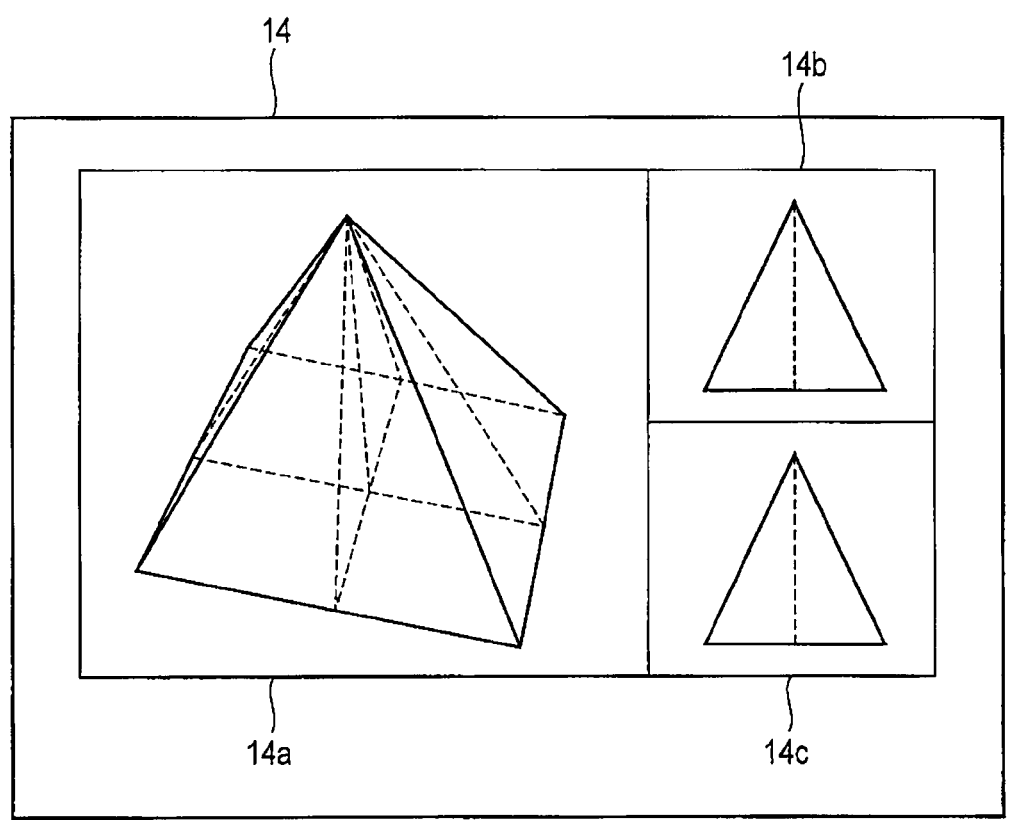
FIG. 9 is a view for explaining a tissue enhancement filtering function according to the fourth embodiment.

FIG. 9 is a view showing an example of a form of simultaneously displaying a plurality of three-dimensional images (a volume rendering image 14a, first multi planar reconstruction image 14b, and second multi planar reconstruction image 14c) on a monitor 14.

The volume data generation unit 32 also generates volume data as an ultrasonic image by using the B-mode image data or the like received from the image generation unit 25. An image processing unit 27 receives volume data from the volume data generation unit 32 and executes predetermined image processing such as volume rendering, multi planar reconstruction (MPR), or maximum intensity projection (MIP) based on these data.

The tissue enhancement processing unit 26 executes, for example, the speckle processing described in the third embodiment for the ultrasonic image received from the image processing unit 27. At this time, when using, for example, the display form shown in FIG. 9, it is possible to perform speckle reduction processing for at least one of the volume rendering image 14a, first multi planar reconstruction image 14b, and second multi planar reconstruction image 14c. Obviously, the three-dimensional image data to be received from the image processing unit 27 is not limited to the above examples of the volume rendering image 14a, first multi planar reconstruction image 14b, and second multi planar reconstruction image 14c. For example, it is possible to execute this speckle processing for three-dimensional image data obtained by other rendering/reconstruction processing techniques such as surface rendering and maximum intensity projection.

The above arrangement can also obtain the same effects as those of the third embodiment.

Note that the present invention is not limited to each embodiment described above, and constituent elements can be modified and embodied in the execution stage within the spirit and scope of the invention. The followings are concrete modifications.

(1) Each function associated with each embodiment can also be implemented by installing programs for executing the corresponding processing in a computer such as a workstation and expanding them in a memory. In this case, the programs which can cause the computer to execute the corresponding techniques can be distributed by being stored in recording media such as magnetic disks ((Floppy®) disks, hard disks, and the like), optical disks (CD-ROMs, DVDs, and the like), and semiconductor memories.

(2) Each embodiment described above has exemplified the case in which the tissue enhancement filtering function is implemented by using ultrasonic images. However, without being limited to the above case, the tissue enhancement filtering function according to each embodiment described above can be applied to, for example, medical images acquired by medical image diagnostic apparatuses such as an X-ray computed tomography apparatus, magnetic resonance imaging apparatus, and X-ray diagnostic apparatus.

(3) In the third embodiment described above, cross-sections for which speckle reduction processing is executed are planes intersecting the central axis of an ultrasonic scanning region. However, without being limited to this example, speckle reduction processing can be performed for arbitrary cross-sections in a three-dimensional space.

Various inventions can be formed by proper combinations of a plurality of constituent elements disclosed in the above embodiments. For example, several constituent elements may be omitted from all the constituent elements in each embodiment. In addition, constituent elements of the different embodiments may be combined as needed.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus comprising:
processing circuitry configured to:
calculate directions of edges in a local region within one ultrasonic image representing a two-dimensional image, sizes of the edges in the local region, and directional uniformity of the edges in the local region, the directional uniformity of the edges representing variability of the directions of the edges in the local region;
calculate a composite coefficient by using a first coefficient representing the sizes of the edges and a second coefficient representing the directional uniformity of the edges, the composite coefficient being a larger coefficient between the first coefficient and the second coefficient or an additional value of the first coefficient and the second coefficient;
calculate a filtering coefficient for a region corresponding to the local region based on the composite coefficient; and
perform filtering processing for sharpening or smoothing the ultrasonic image with respect to the ultrasonic image by using the filtering coefficient,
wherein the processing circuitry is further configured to:
acquire a data set with respect to a second-order derivative of the pixel value in the local region or a spatial derivative of a high-frequency component of a pixel value in the local region;
calculate a first eigenvalue and a second eigenvalue from a covariance matrix of the acquired the data set; and
calculate the directional uniformity based on a contribution ratio of the second eigenvalue.

2. The ultrasonic diagnostic apparatus of claim 1, wherein the processing circuitry comprises an anisotropic nonlinear diffusion filter.

3. The ultrasonic diagnostic apparatus of claim 2, wherein the processing circuitry calculates the composite coefficient based on maximum values or sums of the sizes and directional uniformity of the edges, and
the processing circuitry is further configured to execute the filtering processing upon changing each eigenvalue of a diffusion tensor of the anisotropic nonlinear diffusion filter based on the composite coefficient.

4. The ultrasonic diagnostic apparatus of claim 1, wherein the processing circuitry is further configured to calculate directions of the edges and sizes of the edges based on spatial derivatives of changes in pixel value in the local region.

5. The ultrasonic diagnostic apparatus of claim 1, wherein the processing circuitry is further configured to calculate a spatial derivative of a pixel value in the local region or a first vector by performing spatial differentiation of a high-frequency component of a pixel value in the local region,
calculate at least a first eigenvalue of a structure tensor or a first eigenvalue of a covariance matrix of data in the local region by using the first vector, and
calculate a size of the edge based on the first eigenvalue or a difference between the first eigenvalue and another eigenvalue.

6. The ultrasonic diagnostic apparatus of claim 1, wherein the processing circuitry is further configured to calculate a second-order spatial derivative of a pixel value in the local region or a second vector by performing spatial differentiation of a high-frequency component of a pixel value in the local region,
calculates at least a first eigenvalue of a structure tensor or a first eigenvalue of a covariance matrix of data in the local region by using the second vector, and
calculates a size of the edge based on the first eigenvalue or a difference between the first eigenvalue and another eigenvalue.

7. A medical image processing apparatus comprising:
a memory configured to store a medical image acquired by a medical image diagnostic apparatus; and
processing circuitry configured to:
calculate directions of edges in a local region within one ultrasonic image representing a two-dimensional image, sizes of the edges in the local region, and directional uniformity of the edges in the local region, the directional uniformity of the edges representing variability of the directions of the edges in the local region;
calculate a composite coefficient by using a first coefficient representing sizes of the edges and a second coefficient representing the directional uniformity of the edges, the composite coefficient being a larger coefficient between the first coefficient and the second coefficient or an additional value of the first coefficient and the second coefficient;
calculate a filtering coefficient for a region corresponding to the local region based on the composite coefficient; and
perform filtering processing for sharpening or smoothing the ultrasonic image with respect to the ultrasonic image by using the filtering coefficient, wherein the processing circuitry is further configured to:
acquire a data set with respect to a second-order derivative of the pixel value in the local region or a spatial derivative of a high-frequency component of a pixel value in the local region;
calculate a first eigenvalue and a second eigenvalue from a covariance matrix of the acquired the data set; and
calculate the directional uniformity based on a contribution ratio of the second eigenvalue.

8. The medical image processing apparatus of claim 7, wherein the processing circuitry comprises an anisotropic nonlinear diffusion filter.

9. The medical image processing apparatus of claim 8, wherein the processing circuitry is further configured to calculate the composite coefficient based on maximum values or sums of the sizes and directional uniformity of the edges, and
the processing circuitry is further configured to execute the filtering processing upon changing each eigenvalue of a diffusion tensor of the anisotropic nonlinear diffusion filter based on the composite coefficient.

10. The medical image processing apparatus of claim 7, wherein the processing circuitry is further configured to calculate directions of the edges and sizes of the edges based on spatial derivatives of changes in pixel value in the local region.

11. The medical image processing apparatus of claim 7, wherein the processing circuitry is further configured to calculate a spatial derivative of a pixel value in the local region or a first vector by performing spatial differentiation of a high-frequency component of a pixel value in the local region,
calculate at least a first eigenvalue of a structure tensor or a first eigenvalue of a covariance matrix of data in the local region by using the first vector, and
calculate a size of the edge based on the first eigenvalue or a difference between the first eigenvalue and another eigenvalue.

12. The medical image processing apparatus of claim 7, wherein the processing circuitry is further configured to calculate a second-order spatial derivative of a pixel value in the local region or a second vector by performing spatial differentiation of a high-frequency component of a pixel value in the local region,
calculate at least a first eigenvalue of a structure tensor or a first eigenvalue of a covariance matrix of data in the local region by using the second vector, and
calculate the directional uniformity based on the first eigenvalue or a difference between the first eigenvalue and another eigenvalue.

13. A medical image processing method comprising:
calculating, by processing circuitry, directions of edges in a local region within one medical image acquired by a medical image diagnostic apparatus, sizes of the edges in the local region, and directional uniformity of the edges in the local region, the directional uniformity of the edges representing variability of the directions of the edges in the local region, the medical image representing a two-dimensional image;
calculating, by the processing circuitry, a composite coefficient by using a first coefficient representing the sizes of the edges and a second coefficient representing the directional uniformity of the edges, the composite coefficient being the larger coefficient between the first coefficient and the second coefficient or the additional value of the first coefficient and the second coefficient;
calculating, by the processing circuitry, a filtering coefficient for a region corresponding to the local region based on the composite coefficient; and
performing filtering processing, by the processing circuitry, for sharpening or smoothing the medical image with respect to the medical image by using the filtering coefficient,
wherein the method further comprises:
acquiring, by the processing circuitry, a data set with respect to a second-order derivative of the pixel value in the local region or a spatial derivative of a high-frequency component of a pixel value in the local region;
calculating, by the processing circuitry, a first eigenvalue and a second eigenvalue from a covariance matrix of the acquired the data set; and
calculating, by the processing circuitry, the directional uniformity based on a contribution ratio of the second eigenvalue.

\* \* \* \* \*